United States Patent [19]

Hool

[11] Patent Number: 5,269,176
[45] Date of Patent: Dec. 14, 1993

[54] METHOD FOR DETERMINING LIQUID/LIQUID INTERFACIAL TENSION AND DYNAMIC INTERFACIAL TENSION REDUCTION

[75] Inventor: Kevin O. Hool, Midland, Mich.

[73] Assignee: The Dow Chemical Company, Midland, Mich.

[21] Appl. No.: 922,903

[22] Filed: Jul. 31, 1992

Related U.S. Application Data

[63] Continuation-in-part of Ser. No. 610,197, Nov. 5, 1990, abandoned.

[51] Int. Cl.$^5$ .............................................. G01N 13/02
[52] U.S. Cl. ................................... 73/64.52; 73/64.48
[58] Field of Search ................ 73/64.48, 64.52, 61.43, 73/61.44

[56] References Cited

U.S. PATENT DOCUMENTS

| | | | |
|---|---|---|---|
| 3,913,385 | 10/1975 | Jobe | 73/61.43 |
| 4,646,562 | 3/1987 | Cronan | 73/64.52 |
| 4,697,451 | 10/1987 | Matteson | 73/64.52 |

Primary Examiner—James C. Housel
Assistant Examiner—L. M. Crawford

[57] ABSTRACT

A method is disclosed for providing data useful in evaluating the dynamics of surfactants used to reduce interfacial tension in a system having two immiscible liquids and one or more surfactants. The method involves rapidly growing a drop of a first liquid in the second liquid, but stopping the flow of the first liquid at some point before the drop detaches. The time it takes for the drop to form and detach is then measured. This process is repeated for different volume drops. The drop lifetimes can then be plotted against drop volumes, resulting in a curve which is related to the diffusional coefficient and concentration for the surfactant in the particular liquid/liquid system.

8 Claims, 3 Drawing Sheets

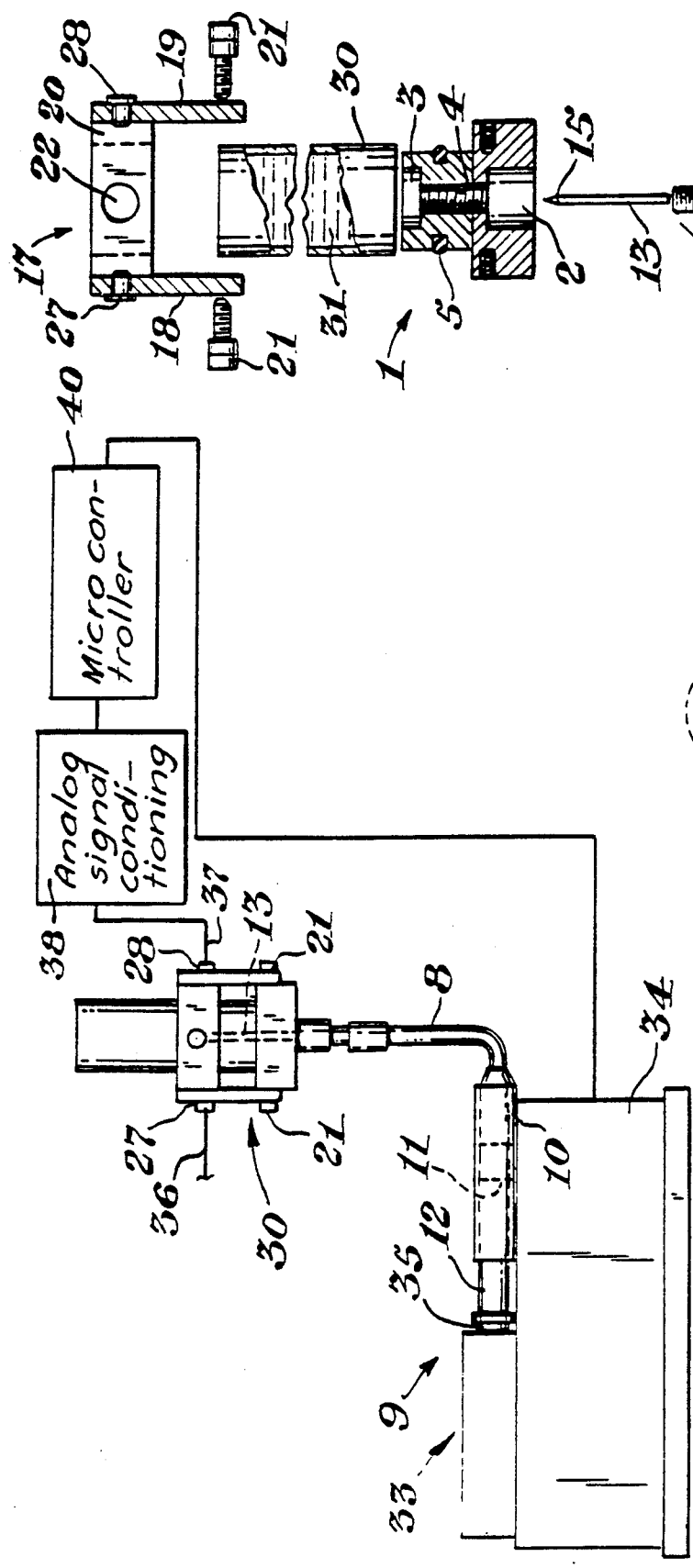
Fig. 1
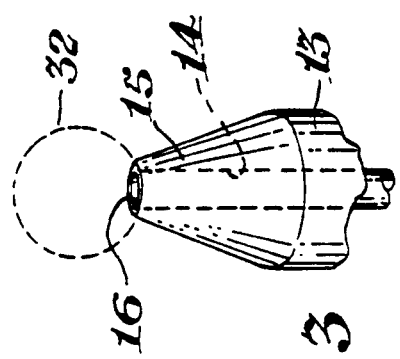
Fig. 2
Fig. 3

METHOD FOR DETERMINING LIQUID/LIQUID INTERFACIAL TENSION AND DYNAMIC INTERFACIAL TENSION REDUCTION

CROSS-REFERENCE TO RELATED APPLICATION

This application is a continuation in part of application Ser. No. 07/610,197, filed Nov. 5, 1990, now abandoned.

BACKGROUND OF THE INVENTION

This invention relates to a method for determining liquid/liquid interfacial tension and evaluating the dynamics of interfacial tension reduction, such method being especially applicable for use in ascertaining the effectiveness of surfactants in reducing interfacial tension between immiscible liquids.

Several techniques presently exist for measuring liquid/liquid interfacial tension to predict surfactant performance. Among them are the spinning drop method, the shear field method, the electric field method, the duNouy ring method, the sessile/pendant drop method, and the drop weight method. Of the methods referred to above the drop weight method is the most similar to the methods disclosed herein, but the methods according to the invention are considerably simpler and more effective for their purpose than is the drop weight method.

In the drop weight method of measuring interfacial tension the weight of each drop is measured in a laborious manner: after each liquid drop has formed and detached, the reservoir of liquid being dispersed by the surfactant is manually weighed. The difference in weight before and after the drop detachment is assumed to be the drop weight. This approach is labor intensive and subject to high probability of producing erroneous data due to human intervention and manipulation.

The drop weight method relies upon Tate's Law extended by the Scheele and Meister development work and modified by Harkin's correction factor due to the necessity of accounting for the fluid volume remaining attached to the dispensing fluid orifice after detachment of each liquid drop. Tate's Law, as modified by Scheele and Meister, is applicable only in those cases in which no surfactant is present in the liquid into which the drop is dispensed and the Harkin's correction is applied to account for liquid left at the dispensing orifice following detachment of a drop.

None of the known methods referred to above for measuring liquid/liquid interfacial tension provides any information with respect to the dynamic aspects of interfacial tension reduction of a liquid/liquid interface by a surfactant. In the methods disclosed herein, however, a measure of the dynamic aspects of such interfacial tension reduction is obtainable.

Among the objects of the present invention is to simplify the measurement of liquid/liquid interfacial tension primarily for the purpose of evaluating the effectiveness of surfactants on various immiscible liquids.

Another object of the invention is to provide a method for the evaluation of the dynamic characteristics of interfacial tension reduction due to the presence of surfactants.

SUMMARY OF THE INVENTION

The interfacial tension between immiscible liquids can be measured according to the invention by forming and counting drops of one liquid detached from a dispensing nozzle submerged in another liquid, the tip of such nozzle having a geometry which avoids a varying wetting profile thereby allowing reproducible drop formation and detachment. Accordingly, it is possible to determine accurately the liquid/liquid interfacial tension without having to use the Harkin or other correction factor. The invention is therefore particularly adapted for predicting the effectiveness of a surfactant in reducing the liquid/liquid interfacial tension. For the purposes of this invention "surfactant" includes anything which is capable of reducing the interfacial tension between two liquids.

The invention provides for the dispensing of a first drop-forming liquid into a second, immiscible liquid at a uniform flow rate sufficient to enable drops of the first liquid to be formed in the second liquid. Either or both of the liquids may contain a surfactant which reduces interfacial tension between the drop and the liquid into which the drop is introduced.

The drop-forming phase or liquid is dispensed through a tube having a nozzle that is immersed in a second liquid contained in a vessel, such second liquid hereinafter sometimes being referred to as a continuous phase. The surface area of the nozzle tip which surrounds the dispensing nozzle is made as close to a razor edge as possible, consistent with machining limitations to avoid irregularities, so as to expose as little area as possible to wetting by the contents of the vessel, thereby providing a constant circumference of the attachment of the drop to the nozzle tip regardless of the liquids used. If the liquid phase from which the drops are formed is of lower density than that of the liquid of the continuous phase into which the drops are dispensed, then the nozzle will be directed upwards and the drops will rise. If the drop-forming liquid phase is of greater density than that of the continuous phase into which the drops are dispensed, then the nozzle will be directed downwards and the drops will descend. In either case, the number of drops produced may be counted.

The dispensing of the drop-forming liquid into the continuous phase is effected at such a rate of flow as to avoid any appreciable contribution to drop detachment due to momentum. As a consequence, the detachment of each drop from the nozzle will be due primarily to the force balance between the adherence force (defined as the product of the interfacial tension times the circumference of the nozzle tip) and a separation force (defined as the product of the drop volume times the difference in densities between the two liquids and the gravity constant).

The invention also provides a method of evaluating the diffusional characteristics of a particular surfactant in a given liquid/liquid system. The method can be carried out using the apparatus of the invention and involves rapidly growing a drop of a first liquid in the second liquid, but stopping the flow of the first liquid at some point before the drop detaches. The time it takes for the drop to detach is then measured. This process is repeated for different volume drops. The drop lifetimes can then be plotted against drop volumes, resulting in a curve which is related to the diffusion coefficient and concentration for the surfactant in the particular liquid/liquid system.

BRIEF DESCRIPTION OF THE DRAWINGS

Apparatus for practicing the invention is disclosed in the accompanying drawings, wherein:

FIG. 1 is a side elevational and diagrammatic view of the apparatus;

FIG. 2 is a fragmentary, enlarged, exploded view of some of the components of the apparatus shown in FIG. 1;

FIG. 3 is a fragmentary, greatly enlarged isometric view, partly in section, of a nozzle forming part of the invention;

DETAILED DESCRIPTION OF THE INVENTION

Figure 4:
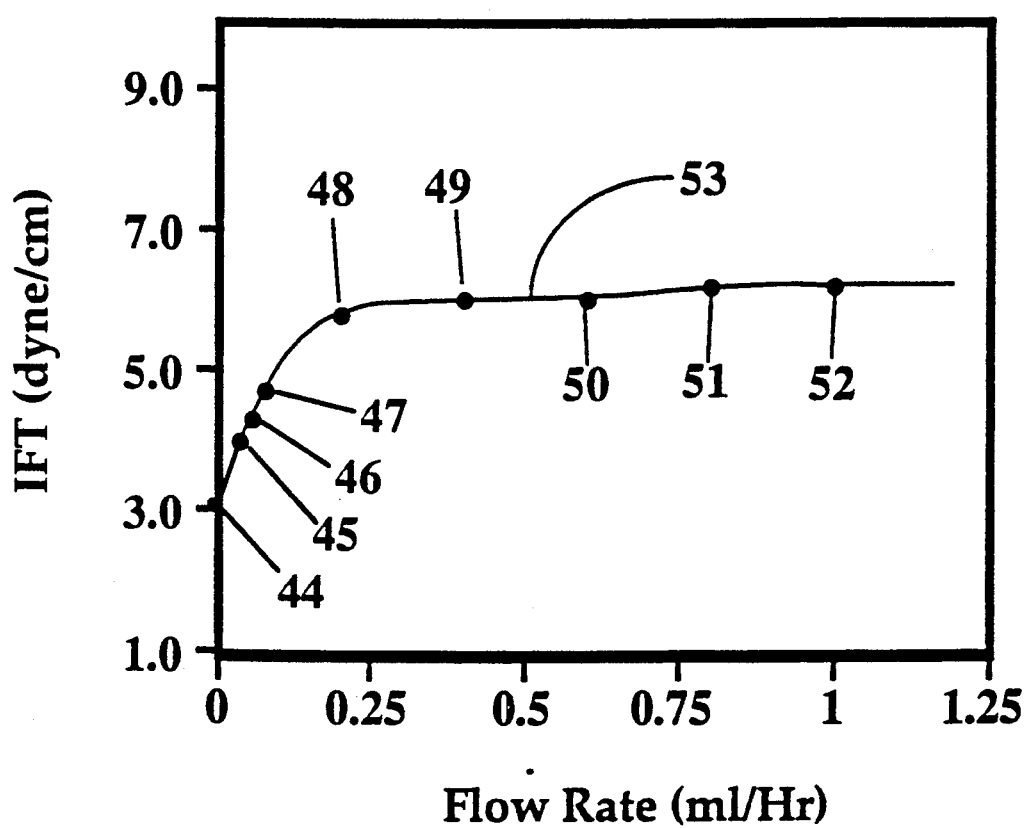
FIG. 4 is a diagram illustrating the dynamic effects of interfacial tension reduction as a result of varying the rate of flow of dodecane into water containing sodium lauryl sulfate.

Apparatus constructed in accordance with a preferred embodiment of the invention comprises a manifold block 1 having a passageway running therethrough, as seen in FIG. 2. The passageway comprises an inlet port 2, an outlet port 3, and a threaded area 4 between the outlet and the inlet ports. The manifold block 1 is comprised of a cylindrical portion adapted for holding an O-ring 5, and a larger base portion. A transparent tube 30 is located around the cylindrical portion and sealed by the o-ring 5 so that the tube 30 may be filled with the continuous phase liquid. All of the parts are formed from materials which are compatible with each other and inert to the liquids being used.

Fitted into the inlet port 2 is an inlet nipple 7 to which is coupled one end of a liquid delivery tube 8, the opposite end of which is coupled to a syringe 9 having a barrel 10 within which is accommodated a supply of a drop-forming liquid and a reciprocating piston 11 fixed to an operating stem 12. The inlet nipple 7 is preferably comprised of an untapped Upchurch Finger-Tight ® fitting 6 which is connected to the liquid delivery tube 8 at one end, and a tapped Upchurch Finger-Tight ® fitting 26 which is adapted to fit into the threaded area 4 of the manifold block. The untapped fitting 6 is adapted to fit within the inlet of the tapped fitting 26.

A tubular discharge member 13, formed preferably of tungsten carbide, is separably secured at the outlet end of the tapped fitting 26. The member 13 has a bore 14 in communication with the passage 4. The member 13 terminates at its free end in a preferably frustoconical nozzle 15. As is best shown in FIG. 3 the free end of the nozzle terminates in an annular, convex tip 16 the radial thickness of which is substantially less than the radial thickness of any other portion of the wall of the member 13 or the nozzle 15. The area of the surface 16 is exaggerated in FIG. 3. The surface of the tip 16 ideally is a razor edge for the purpose of defining a constant circumference of the nozzle outlet, but machining limitations cause the surface to be of finite area. Furthermore, the entire tubular discharge member 13 could be of razor edge thickness, but due to current materials and machining limitations the frustoconical configuration is preferred.

A sensor supporting frame 17 comprises a pair of parallel legs 18 and 19 joined at their upper ends by a horizontal section 20. The sensor supporting frame 17 is attached to the base portion of the manifold block with set screws 21.

The horizontal section 20 has a vertically aligned cylindrical hole passing therethrough, the hole being adapted to closely fit over the outside of the transparent tube 30. The horizontal section also includes a pair of diametrically opposed apertures adapted for the accommodation of optical sensing means. The optical sensing means comprises a light emitting diode 27 and a photodiode receiver 28, arranged so that the light emitting diode 27 transmits a beam along a horizontal path toward the photodiode 28. The horizontal section 20 of the sensor supporting frame 17 also contains a sight hole 22, to allow a visual inspection of the drops as they are formed and detached.

The apparatus is assembled such that the transparent tube 30 is placed over the O-ring 5, and the frame 17 is attached to the manifold block 1 with the set screws 21. Then the transparent tube 30 is filled with a continuous phase or first liquid 31 to a level which is above the sensor supporting frame 17. The syringe 9 contains a second, drop-forming liquid that is immiscible with the first liquid 31. Displacement of the piston 11 inwardly of the barrel 10 will cause liquid to be delivered from the syringe through the nozzle 15 via the line 8, the inlet fitting 7, the passages 3 and 4, and the bore 14 of the member 13.

Alternatively, if the second, drop-forming liquid is more dense than the first liquid, the apparatus should be assembled upside down from the apparatus in FIG. 1. In this situation, the transparent tube 30 should be closed at one end, filled with the first liquid and then the apparatus lowered nozzle-first into the transparent tube 30.

The flow rate at which the liquid from the syringe is delivered through the nozzle tip 16 should be such that the discharged liquid forms successive drops 32, rather than a stream. Preferably, the flow rate is in a range the upper value of which is such that fluid momentum has no appreciable effect on drop detachment from the nozzle. The rate of flow of liquid from the supply in the syringe 9 conveniently may be regulated by a syringe pump 33 having a base 34 within which is a driving mechanism having a reciprocating driver 35 coupled to the syringe plunger 12. A suitable syringe pump is that manufactured by Harvard Apparatus (South Natick, Mass.), Model No. 44. The pump 33 is preferably controlled by a microprocessor based microcontroller 40 so that the flow of the first liquid may be precisely controlled.

The optical diodes 27 and 28 are coupled by suitable wiring 36 and 37 to a source of electrical energy and to a conventional electrical pulse processor and amplifier 38 which, in turn, is electrically coupled to a microcontroller 40. The signal processor and amplifier includes known analog and digital electronic circuitry. The light source 27 may be an infrared light emitting diode sold by General Electric Company under the designation LED55C, and the receiver diode 28 may comprise a photodiode sold by Motorola, Inc., under the designation MRD500. The microcontroller 40 can be the same microcontroller which preferably controls the pump 33. One suitable microcontroller is a microprocessor based microcontroller sold by Basicon with the part number designation MC-li.

The liquid 31 in the vessel 30 may be water or any one of a number of other liquids. The liquid in the syringe 9 may be oil or any one of a number of other liquids that essentially are immiscible with the liquid in the vessel 30. For purposes of evaluating surfactants at least one of the liquids should contain a known amount of a surfactant that is chosen for its ability to reduce the liquid/liquid interfacial tension existing between the two immiscible liquids. For purposes of this invention, "surfactant" includes any substance that affects the interfacial tension between the two liquids.

In the continuous-flow method of use, liquid in the syringe 9 is dispensed therefrom by constant speed displacement of the piston 11 so as to deliver such liquid at a substantially constant rate of flow to and through the bore 14 of the nozzle 15. As liquid emerges from the nozzle tip 16 it will form successive drops 32. If the liquid constituting each drop 32 has a lower density than that of the liquid 31, the drop will enlarge in size until the force of buoyancy overcomes the adherence force of the nozzle surface 16 and causes it to separate from the nozzle 15 and rise between the optical devices 27 and 28. Such movement of the drop 32 will interrupt the beam of light transmitted from the emitter 27 to the receiver 28, thereby generating a pulse which is transmitted to the signal processor and amplifier 38 where it is amplified and transmitted to the microcontroller 40. The microcontroller 40 then starts a timer. Once the timer has been started, the pulses generated by interruption of the light beam by successive drops 32 will actuate the counter so as to count the number of drops discharged from the nozzle. The timer can be set to be operative until a selected number of drops, such as 10, has been counted, or to remain operative for a selected time period regardless of the number of drops counted.

The precise volume of liquid discharged from the syringe easily is ascertained by automatic or manual calculations based on the displacement of the piston 11.

The interfacial tension between the two liquids can be determined from the amount of time required to form a selected number of drops at a constant flow rate. As is well known, the more effective a surfactant is in reducing interfacial tension, the smaller are the drops that will be detached from the nozzle. Thus, if one surfactant, or concentration thereof, enables the same number of drops to be formed in a lesser time period from liquid dispensed at a constant flow rate from the syringe than can be formed under the same conditions but using another surfactant or concentration thereof, the one surfactant is more effective in reducing interfacial tension at that flow rate.

It thus is possible to ascertain the effectiveness of a surfactant at a particular constant flow rate simply by comparing the time required to produce a selected number of drops from the dispensed liquid with the number of drops formed under the identical conditions, but using another surfactant or a different concentration of the same surfactant assuming, of course, that the densities of the two liquids remain relatively constant or that any change in the relative densities is known. In those instances in which automation is not required, the counting of the drops may be effected visually and the time period can be measured manually. It is preferred, however, to make use of the microcontroller 40 for automatic timing and for making the calculations according to Tate's law.

Rather than limiting the counting of drops to a fixed, selected number of drops, it is possible to count the number of drops that are produced at a constant flow rate in a selected period of time. In this instance the more effective surfactant will cause a greater number of drops to be formed in the same time period for the reason that the more effective surfactant will cause a greater number of drops to be produced from a given volume of dispensed liquid.

The more effective surfactant at one rate of flow is not always the more effective surfactant at a different rate of flow, however. This phenomenon is partly explained by the differences in mass transfer of the surfactants to the interface. Mass transfer rates are primarily dependent on the rates of diffusion of the various surfactants within the particular interfacial system. A surfactant which is very effective at low flow rates (near equilibrium conditions) may not be effective at higher flow rates, if the surface area of the drop is growing faster than the rate at which the surfactant can be conveyed to the newly formed surface area. Accordingly, in order to more fully evaluate a surfactant's overall effectiveness, it is necessary to assess the diffusional characteristics of the surfactant.

A surfactant's diffusional characteristics can be evaluated using the same apparatus as described above in a "stopped-flow" mode. Briefly, in the stopped-flow mode drops are formed by flowing the first liquid out of the nozzle means into the second liquid as before. The flow is stopped, however, before the drop detaches. The drop will remain at the tip of the nozzle means until enough surfactant has diffused to and accumulated at the interface to sufficiently reduce the tension. The larger the drop in a given system the less the tension must be reduced before the drop will detach from the nozzle means. A plurality of volumes of the first liquid can be dispensed and plotted against the resultant drop lifetimes giving an indication of the diffusional characteristics of the particular surfactant at that particular concentration.

More specifically, the first step is preferably to determine the maximum volume of a drop in the given liquid/liquid system, so that the volume of the first liquid which may be dispensed without causing the drop to detach from the nozzle means can be determined. For purposes of this invention, the maximum volume is defined as the average volume of drops formed when the flow rate of the first liquid into the second liquid is approximately equal to the maximum value of the preferred range (i.e. the average volume of drops produced when the first liquid is flowing at a rate near the rate at which fluid momentum begins to have an appreciable effect on drop detachment from the nozzle). Preferably, the maximum volume is obtained by determining the highest flow rate before momentum begins to have an effect, and then using the apparatus and the continuous flow method of the invention to determine the average volume of each of the drops produced at that flow rate. Alternatively, the average volume of drops produced at a particular flow rate known to be near the upper range can be used, without actually determining that it is the highest flow rate before momentum begins to have an effect.

Next, a preselected volume of the first liquid is rapidly dispensed from the nozzle thereby forming a drop. The preselected volume should be less than the maximum volume determined above to deter the drop from prematurely detaching. Once the preselected amount of the first liquid has been dispensed, the flow is stopped. Thus, a drop having a fixed volume will be located at the tip of the nozzle. This drop will remain at the tip of the nozzle until enough surfactant has diffused to and accumulated at the interface to reduce the interfacial tension enough so that the gravitational (or buoyant)

forces are larger than the interfacial tension, thereby causing the drop to detach. The lifetime of this drop, from beginning of formation to detachment, is carefully measured, preferably by the microcontroller 40. The microcontroller 40 can also be used to control the pump 33 in order to precisely deliver the preselected volume of the first liquid at a reproducible rate.

In the stopped-flow mode of this invention the first liquid is rapidly dispensed from the nozzle means. Ideally, the liquid would be dispensed instantaneously, thereby eliminating all factors which might cause the drop to detach from the nozzle except for the diffusion and accumulation of the surfactant at the interface. However, as this is not currently possible, the drop is most advantageously formed by flowing the first liquid out of the nozzle at a rate near the rate at which momentum begins to have an appreciable effect on the drop detaching from the nozzle. As long as the flow rate is fast enough so that the flow of the liquid can be stopped before the drop detaches from the nozzle, however, some information about the surfactant's diffusional characteristics can be obtained.

The process of stopping the flow of the first liquid after a preselected volume has been dispensed is then repeated for different volumes, each less than the maximum drop volume. When the drop lifetimes are plotted against the drop volumes (which can be expressed relative to the maximum drop volume) a curve results, the shape of which is indicative of the diffusional characteristics of the surfactant. By forming the drop rapidly, the surface area of the drop remains constant over most of the lifetime of the drop, reducing the affects of factors other than diffusion which may affect the reduction of interfacial tension. Consequently, in the stopped-flow mode, the primary factor accounting for differences in the shapes of the curves produced is the diffusional characteristics of the particular surfactant at that particular concentration.

The best evaluation of a surfactant's effectiveness is obtained when the continuous flow and the stopped-flow methods are combined. When the system is set up for continuous flow, the overall effectiveness of the surfactant at any particular flow rate can be obtained, and when the system is set up in the stopped-flow mode, information about the rates of diffusion for the particular surfactant can be obtained.

A particularly important characteristic of the invention is the use of a nozzle 15 having as small a surface area at its tip 16 as is possible. The advantage is that such a small surface area provides little area that can be wetted by either of the liquid phases and/or the components thereof, thereby providing a substantially constant circumference for drop formation at the nozzle tip. The detachment of each drop from the nozzle is dependent on the force balance between the inherent adherence force between the drop and the nozzle and the separation force. Thus, when the density of the drop-forming liquid is less than that of the liquid 31, each drop will expand until its buoyancy overcomes the adherence force between the drop and the nozzle tip, and when the density of the liquid introduced into the liquid 31 is higher than that of the latter, each drop will expand until the force of gravity acting thereon exceeds the adherence force provided by the nozzle tip 16. The adherence force in each instance will be dependent on the interfacial tension between the liquids acting on the nozzle tip 16.

Because of the uniformity in size of successive drops formed by the apparatus constructed and operated in accordance with the invention, there is no necessity of utilizing Harkin's or any other correction factor in determining the interfacial tension between the two liquids. Instead, the important considerations are to maximize the stability of the flow rate, and to minimize the area of the nozzle outlet surface. The average volume of each drop (and therefore the interfacial tension) formed in the continuous flow mode of the invention can then be calculated given the diameter of the nozzle outlet, the number of drops counted and the time period during which the drops were counted. Uniformity in successively formed drops also helps in the stopped-flow mode, as the time it takes for a series of nearly identical drops to detach can be averaged, thereby potentially producing a more reliable result than would be obtained from a single data point.

In those instances in which the method utilizes ascending drops, as is shown in FIGS. 1-3, it is desirable to avoid the accumulation of the drops at the surface of the liquid in the vessel 30. This may be accomplished by partially immersing a collector (not shown), such as an overturned test tube, in the path of ascending drops 32 so as to enable the latter to be collected in the test tube. The test tube may be supported by a bracket (not shown) secured to the frame 17.

The apparatus and methods disclosed herein provide the capability of obtaining information with respect to the characteristics of interfacial tension reduction as a function of time of the liquid/liquid interface by the use of a surfactant. The disclosed methods and apparatus provide for a variable, selectable, controlled rate of growth of the interfacial area between a drop and the immiscible liquid in which the drop is accommodated. This is achieved by the appropriate selection of flow rates of liquid from the syringe over a range of 0-2 mL/Hr for most systems.

Whenever a surfactant is present in a liquid/liquid system, the interfacial tension value is not constant at different flow rates because such value depends on the age of the interfacial area. For example, if the flow rate of the dispensed liquid is relatively slow, the surfactant has a greater period of time to act on the liquids at their interface. Conversely, if the flow rate is relatively fast, there is less time for the surfactant to act, so larger drops are produced. Evaluating the surfactant in the continuous-flow mode at different flow rates and evaluating the surfactant according to the stopped-flow method of the invention are two ways of ascertaining information relating to the dynamic aspects of interfacial tension reduction.

For any particular liquid/liquid system, the dynamic characteristic of interfacial tension reduction is unique for each different surfactant. It therefore is possible to use the dynamic data to differentiate and evaluate the performance of different surfactants or concentrations thereof. Such information can be more significant than equilibrium based interfacial tension measurements for some purposes, such as the formation and stabilization of emulsions or suspensions.

An example of dynamic analysis using the continuous flow method of this invention of one surfactant used to reduce interfacial tension between water and dodecane is shown in FIG. 4. In this example the surfactant is sodium lauryl sulfate (SLS) at a concentration of 2,500 ppm.

The interfacial tension is plotted on the Y-axis of FIG. 4. The values for the interfacial tension were calculated (using Tate's Law) from the average volume of a selected number of drops formed at the given flow rate. The average volume was calculated by dividing the number of drops formed over a period of time by the amount of fluid dispensed over that same period of time. These values were obtained by the apparatus and methods described above. If preferred, the average volumes of the drops produced at a given flow rate can be placed along the Y-axis, directly with no calculation of the interfacial tension being made.

On the X-axis of FIG. 4 is plotted the rates of flow at which the dodecane is dispensed into the water. It is possible, however, to plot the drop formation rate or frequency on the X-axis.

The point labelled 44, in FIG. 4, represents an extrapolation of the interfacial tension at a zero flow rat (equilibrium) for the system. The point 45 represents the average interfacial tension of 10 drops at a flow rate of 0.04 mL/Hr; the point 46 represents the average interfacial tension of 10 drops at a flow rate of 0.06 mL/Hr; and the points 47, 48, 49, 50, and 52 each represent the average interfacial tensions of 10 drops formed at flow rates of 0.06, 0.20, 0.40, 0.60, 0.80 and 1.0 mL/Hr, respectively. The points 44–52 52 have been connected to form a curve 53.

The slope at any point along the curve 53 represents a measure of the resistance to change in interfacial area due to the presence of the surfactant.

Figure 5:
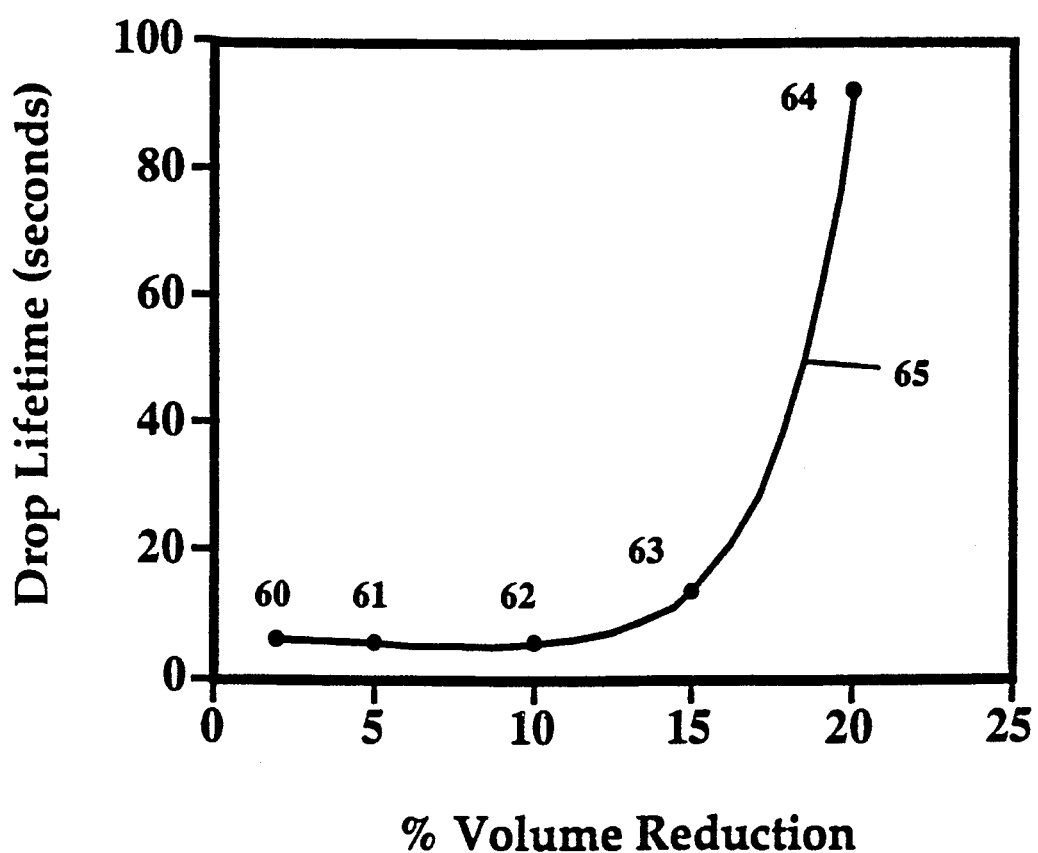
FIG. 5 is a diagram illustrating the diffusional characteristics of sodium lauryl sulfate when used to reduce the interfacial tension between dodecane and water.

Next, the same surfactant (SLS) in the same liquid/liquid system (dodecane into water) was evaluated according to the stopped-flow method of this invention. The results are shown in FIG. 5 wherein the drop lifetime is plotted against the size of the drop when the flow was stopped (presented as a percentage of the volume of the average drop formed when the flow rate is near the maximum value of the preferred ran For this application, 2.10 µl was was determined using a plot such as the continuous flow plot from FIG. 4 to be the drop volume obtained in the system when t rate is near the maximum value of the preferred range (approximately 2.5 ml/hr). Accordingly, a drop having this volume was defined as being 100% to calculate the % volume reductions plotted in FIG. 5. Successively smaller drops (labelled as successively larger reductions), requiring successively larger reductions of interfacial tension before the drop detaches, extend along the X-axis. The lifetimes of these drops are plotted along the Y-axis. Point 60 indicates the average lifetime (5.82 seconds) of 10 drops formed at the selected flow rate of 2.5 ml/hr, while stopping the flow after 98% (2.06 µl) of the volume for the average drop formed at a flow rate near the maximum of the preferred range (2.10 µl)was dispensed. Thus when the flow was stopped, a drop having a 2% reduction in volume from the maximum drop volume was formed. Points 61–64 represent the average lifetimes of drops having volume reductions of 5%, 10%, 15%, and 20%, respectively, as compared to 2.10 µl. These points have been connected to form a curve 65. This curve asymptotically approaches a value which corresponds to the volume of a drop at equilibrium. The shape of the curve is governed by the diffusion coefficient and concentration for the surfactant in the particular liquid/liquid system.

Data corresponding to those shown in FIGS. 4 and 5 can be obtained under identical conditions for the same liquids but using a different surfactant or a different concentration of the same surfactant. The resulting data then can be compared with one another to indicate which surfactant, or concentration thereof, is more effective in the dynamic process of interfacial tension reduction.

It should be realized by one of ordinary skill in the art that the invention is not limited to the exact construction or method illustrated above, but that various changes and modifications may be made without departing from the spirit and scope of the invention as described within the following claims.

What is claimed is:

1. A method of evaluating surfactants comprising the steps of:
   (a) providing a first liquid, a second liquid which is immiscible in the first liquid and one or more surfactants dispersed within at least one of the liquids;
   (b) flowing the first liquid out of a nozzle means into the second liquid at a preselected constant rate, such that a drop of the first liquid is formed within the second liquid;
   (c) stopping the flow of the first liquid after a preselected volume of the first liquid has been dispensed, said preselected volume being small enough so that the drop does not detach form the nozzle means before the flow is stopped;
   (d) allowing the drop to remain at the end of the nozzle until the surfactant in the liquids has reduced the interfacial tension enough to cause the drop to detach form the nozzle means;
   (e) measuring the time it takes for the drop to detach from the nozzle means;
   (f) repeating steps (b) through (e) for a plurality of different preselected volumes dispensed at the same preselected constant rate of flow; and
   (g) evaluating the effectiveness of the surfactant in the liquids based on the measured times in relation to the preselected volume.

2. The method of claim 1 wherein the preselected constant rate of flow of the first liquid approaches a rate of flow where fluid momentum begins to have an appreciable effect on drop detachment from the nozzle means.

3. The method of claim 1 wherein the times obtained in step (e) are plotted against the preselected volumes.

4. The method of claim 3 wherein the preselected volumes are expressed as a percentage of the volume at which a drop formed at the preselected constant rate will detach from the nozzle means without stopping the flow.

5. The method of claim 1 wherein the first liquid contains a surfactant.

6. The method of claim 1 wherein the second liquid contains a surfactant.

7. The method of claim 1 wherein both the first and the second liquids contain a surfactant.

8. The method of claim 1 wherein measuring the time it takes for the drop to detach from the nozzle means includes measuring the time it takes to form the drop.

* * * * *